United States Patent
Bär et al.

(10) Patent No.: US 7,688,067 B2
(45) Date of Patent: *Mar. 30, 2010

(54) PROBE FOR ELECTRICAL MEASUREMENT METHODS AND USE OF A FLEXIBLE PROBE FOR PRODUCTION OF A RIGID PROBE

(75) Inventors: Ludwig Bär, Erlangen (DE); Werner Heinrich, Bärenklau (DE)

(73) Assignee: Siemens Aktiengesellschaft, Munich (DE)

( * ) Notice: Subject to any disclaimer, the term of this patent is extended or adjusted under 35 U.S.C. 154(b) by 657 days.

This patent is subject to a terminal disclaimer.

(21) Appl. No.: 10/501,724

(22) PCT Filed: Dec. 23, 2002

(86) PCT No.: PCT/EP02/14738

§ 371 (c)(1),
(2), (4) Date: Jul. 15, 2004

(87) PCT Pub. No.: WO03/060530

PCT Pub. Date: Jul. 24, 2003

(65) Prior Publication Data

US 2005/0140366 A1     Jun. 30, 2005

(30) Foreign Application Priority Data

Jan. 17, 2002   (EP)   .................. 02001268

(51) Int. Cl.
*G01R 27/26* (2006.01)
*G01N 27/72* (2006.01)

(52) U.S. Cl. ........................ 324/220; 324/239

(58) Field of Classification Search .............. 324/242, 324/236, 237–243, 260–262, 220
See application file for complete search history.

(56) References Cited

U.S. PATENT DOCUMENTS

| 4,863,536 | A | * | 9/1989 | Heidenhain et al. ........... 156/56 |
| 5,315,234 | A | | 5/1994 | Sutton, Jr. et al. |
| 5,389,876 | A | | 2/1995 | Hedengren et al. |
| 5,467,775 | A | | 11/1995 | Callahan et al. |
| 5,510,709 | A | * | 4/1996 | Hurley et al. ................ 324/242 |
| 6,002,251 | A | | 12/1999 | Sun |
| 6,067,002 | A | * | 5/2000 | Fujino et al. ................ 336/200 |
| 6,198,280 | B1 | * | 3/2001 | Hensley et al. .............. 324/237 |
| 6,452,384 | B1 | * | 9/2002 | Becker et al. ................ 324/240 |
| 6,954,065 | B2 | * | 10/2005 | Shoji ........................... 324/240 |
| 7,463,039 | B2 | * | 12/2008 | Bar et al. ..................... 324/600 |

FOREIGN PATENT DOCUMENTS

| DE | 197 48 556 A1 | 5/1999 |
| EP | 0 228 177 A2 | 7/1987 |
| EP | 0 556 557 A1 | 8/1993 |
| JP | 58153157 A | 9/1983 |
| JP | 05069138 A | 3/1993 |
| JP | 05142205 A | 6/1993 |
| JP | 07038956 A | 2/1995 |
| JP | 10197492 A | 7/1998 |
| WO | WO 01/63308 A1 | 8/2001 |

* cited by examiner

*Primary Examiner*—Reena Aurora

(57) ABSTRACT

The invention relates to a probe for electrical measurements and use of a flexible probe to produce an inflexible probe. Conventional probes comprise a substrate which is mechanically rigid. As a result only planar surfaces may be examined with the probe. According to the invention, a probe is flexibly embodied by means of a flexible substrate such that the probe may be adjusted to match various curvature radii of test bodies.

8 Claims, 1 Drawing Sheet

PROBE FOR ELECTRICAL MEASUREMENT METHODS AND USE OF A FLEXIBLE PROBE FOR PRODUCTION OF A RIGID PROBE

CROSS REFERENCE TO RELATED APPLICATIONS

This application is the US National Stage of International Application No. PCT/EP02/14738, filed Dec. 23, 2002 and claims the benefit thereof. The International Application claims the benefits of European Patent application No. 02001268.8 EP filed Jan. 17, 2002, both of the applications are incorporated by reference herein in their entirety.

FIELD OF INVENTION

The invention is based on a probe for electrical measurement methods as claimed and on the use of a flexible probe for production of an inflexible probe as claimed.

BACKGROUND OF INVENTION

DE 197 48 556 A1 discloses a probe for eddy current measurement having ferromagnetic signal amplification, with the signal amplification being produced by a rigid ferritic core. Only test bodies with a planar surface can be measured by a probe which is formed from a rigid substrate on which planar coils are fitted. If the surfaces are uneven, the shape of the probe must be matched to a surface of the test body, otherwise, incorrect measurement values will be obtained.

A probe with eddy current measurement and with ferromagnetic signal amplification for planar test bodies is also known from U.S. Pat. No. 6,002,251.

U.S. Pat. No. 5,389,876 discloses a probe for eddy current measurement, although this produces only weak signals.

SUMMARY OF INVENTION

The object of the invention is thus to specify a probe for electrical measurement methods, which can be used for differently curved surfaces on a test body.

The object is achieved by the probe together with the substrate being flexible.

Further advantageous refinements of the probe according to the invention are mentioned in the dependent claims.

The probe can be matched to radii of curvature of, for example, 50 mm or more.

Flexibility is advantageously achieved by using a substrate that is formed from a flexible sheet, and by advantageously using polyimide for the probe.

By way of example, two in particular planar coils, in particular composed of copper, are advantageously fitted to the flexible sheet as electrical components.

The flexibility of the probe is also maintained by a flexible rear key for the electrical components.

A polymer sheet which is filled with a ferrite is advantageously used for the flexible rear key, advantageously allowing ferromagnetic signal amplification.

Thin flexible metal sheets composed of ferrite may likewise be used. An encapsulation component having ferrite particles can also be used in this case, with the encapsulation compound being easily plastically deformable.

BRIEF DESCRIPTION OF THE DRAWINGS

Exemplary embodiments of the invention are illustrated in a simplified and schematic form in the drawings, in which.

DETAILED DESCRIPTION OF INVENTION

Figure 1:
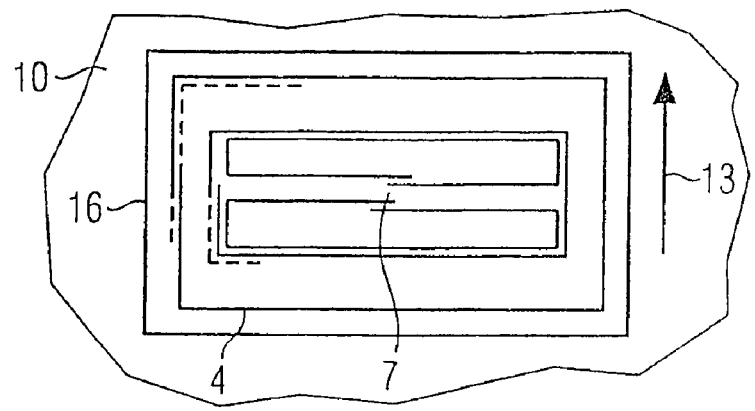
FIG. 1 shows an arrangement of an exciter and a signal coil.

FIG. 1 shows an excitation coil 4 and a signal coil 7 as electrical components arranged on a plane, according to the prior art.

The signal coil 7 is surrounded, for example, by the excitation coil 4. With regard to the further construction of the example of the excitation coil 4, the signal core 7 and an evaluation system using a probe, reference should be made to DE 197 48 556 A1, which is expressly intended to be a part of this disclosure.

The excitation coil 4 and the signal coil 7 are electrically isolated from one another. The signal coil 7 in this example is in the form of a difference probe. The spatial resolution is governed by the distance between the centres of gravity of the two coil elements, the so-called baseline.

The excitation winding 4 surrounds the coil elements of the signal coil 7 symmetrically, for example, so that this ensures compensation for the excitation field.

Exemplary embodiments of probes are:
An XXL probe has a baseline of 3.3 mm, an excitation coil with 21 turns, and a signal coil with 8 turns.
An S probe has a baseline of 2.3 mm, an excitation coil with 9 turns, and a signal coil with 5 turns.

A probe which, inter alia, comprises an excitation coil 4 and a signal coil 7 is moved in a scanning direction 13, identified by an arrow, over a surface of a test body 10 (indicated by a dashed circumferential line), with the probe 1 coming to rest with a contact surface 37 (FIG. 2) on the test body 10. By way of example, the test body 10 contains defects in the form of cracks, which influence a magnetic signal in the excitation coil 4, by which means it is possible to detect the defects in the interior of the test body 10, and on its surface.

Figure 2:
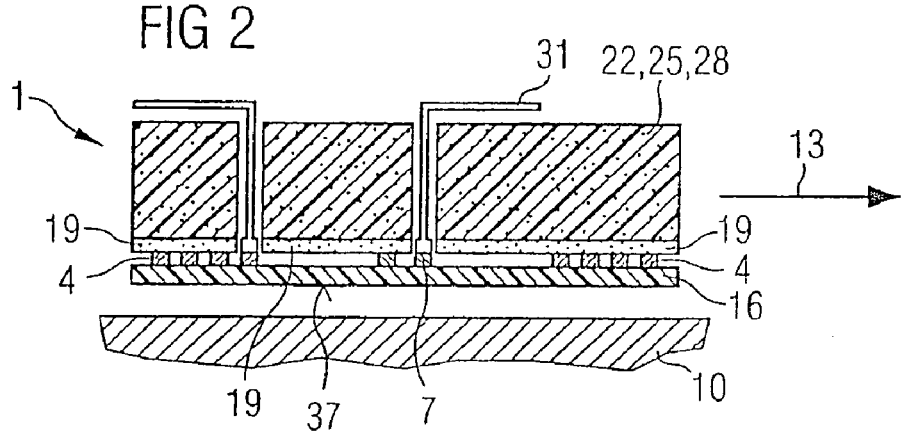
FIG. 2 shows a first exemplary embodiment of a probe according to the invention.

FIG. 2 shows a first exemplary embodiment of a probe 1 for electrical measurement methods according to the present invention. A sheet which is flexible, for example, is used as the substrate 16, which rests directly on the test body. A polyimide sheet is preferably used.

The excitation coil 4 and the signal coil 7 are arranged, for example in a planar form, on the substrate 16, that is to say the coil comprises only one conductor track, which runs only on a plane. The coils 4, 7, as electrical components, can be fitted to the sheet 16 by means of a galvanic process or a wet-chemical method. An adhesive 19, which connects a rear key 22 to the substrate 16, is, but need not necessarily be, applied to the substrate 16 and to and around the coils 4, 7.

The rear key 22 is likewise flexible. A ferrite material (for ferromagnetic signal amplification) with a permeability μ of up to 100 is preferably used as the material for the rear key 22. By way of example, at least one electrical supply line 31 for the coils 4, 7 for a measurement system according to DE 197 48 556 A1 is passed through the rear key 22.

A polymer sheet 25 filled with ferrite particles may be used as the rear key 22.

It is likewise possible to use a thin flexible ferrite metal sheet for signal amplification.

The polyimide sheet 16 has, for example, a thickness of 25 μm, the copper coil has a thickness of 17 μm, the adhesive extends over a thickness of about 30 μm, and the polymer sheet that is filled with ferrite extends over a thickness of 200 to 600 μm.

This layer stack remains sufficiently flexible to allow the layer stack to be matched to different radii of curvature of the test body 10, for example, 50 mm and more, without any problems.

Figure 3:
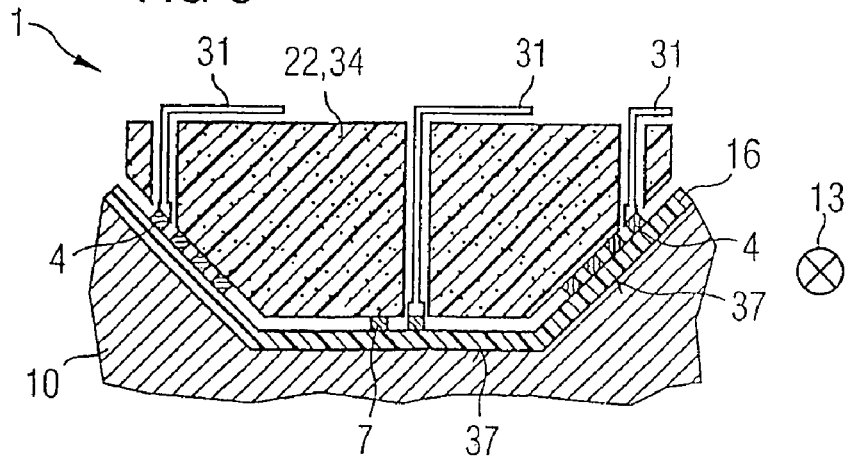
FIG. 3 shows a further exemplary embodiment of a probe designed according to the invention.

FIG. 3 shows a further exemplary embodiment of a planar probe 1 designed according to the invention.

The rear key 22 can also be ensured by means of an encapsulation material 34, in which ferrite powder is mixed. The mean diameter of the ferrite particles is, for example, about 10 μm. The encapsulation compound is and remains easily plastically deformable after a curing process, thus ensuring that the probe 1 is permanently flexible.

An encapsulation probe such as this can also be used in order to produce a rigid probe 1 for specific curved surfaces. In this case, an encapsulation compound 34 is used which can be cured in a state in which it is deformed in this way, such that it can subsequently be plastically deformed only with difficulty, and is thus permanently matched to the contour of specific test bodies 10. The advantage of the method in this case is that a flexible probe 1 is first of all matched to a surface of a test body 10 without any major effort, and the encapsulation compound 34 is subsequently cured, so that there can be no air gap between the contact surface 37 of the sheet 16 and the curved surface of the test body 10 to corrupt the measurement result.

As an electrical measurement method, the probe 1 which, by way of example, has two coils 4, 7 or only one coil as well as the ferromagnetic signal amplification 22, can be used for eddy current measurement which serves, for example, to detect defects in or on metallic components 10.

The invention claimed is:

1. An eddy current measuring device, comprising:
   a flexible base comprising a front surface that comes in contact with a test body;
   a signal coil;
   an excitation coil;
   wherein the signal coil and the excitation coil are arranged in a planar form in a single layer on a rear surface of the flexible base; and
   a flexible rear layer comprising a ferrite particle material that at least partially covers and contacts the signal coil and the excitation coil;
   wherein the flexible base, the signal coil, the excitation coil, and the flexible rear layer are assembled in a flexible stack of layers that remains sufficiently flexible to allow the stack to be variably matched to radii of curvature on a surface of the test body; and
   wherein the flexible base is a flexible sheet with a thickness of about 25 microns, the coils each have a thickness of about 17 microns, and the ferrite particle material extends over a thickness of about 200-600 microns.

2. The device as claimed in claim 1, wherein the sheet is formed from polyimide.

3. The device as claimed in claim 1, wherein at least one of the two coils is made of copper.

4. The device as claimed in claim 1, wherein the flexible rear layer is formed by a polymer sheet filled with ferrite.

5. The device as claimed in claim 1, wherein the flexible rear layer is formed by a plastically deformable encapsulation compound filled with ferrite particles.

6. The device as claimed in claim 1, wherein the device has ferromagnetic signal amplification.

7. An eddy current measuring device, comprising:
   a flexible base formed as a flexible sheet of polyimide;
   a first electrical component connected to the flexible base;
   a second electrical component connected to the flexible base; and
   a rear layer comprising a flexible curable material encapsulating ferrite particles, the rear layer attached to at least one of the electrical components on a curved surface of the rear layer to match a curved surface of a test body;
   wherein the flexible base, the first and second electrical components, and the rear layer collectively form an assembled stack that is flexible after curing of the curable material to variably conform to the curved surface of the test body;
   wherein at least one coil is connected to the flexible base as an electrical component and is a copper coil with a thickness of about 17 microns, the flexible base has a thickness of about 25 microns, the ferrite powder comprises ferrite particles with a mean diameter of about 10 microns, and the flexible curable material extends over a thickness of about 200-600 microns; and wherein the device has ferromagnetic signal amplification.

8. A method of producing a rigid electrical sensing probe from a flexible electrical sensing probe, comprising:
   forming an flexible electrical sensing probe comprising a flexible sheet with a first surface for contact with a test body, an electrical coil attached in a single layer on a second surface of the flexible sheet, and a plastically deformable ferrite powder encapsulation material attached to the second surface of the flexible sheet and/or to the single layer of the electrical coil, to create a multi-layer flexible electrical sensing probe;
   matching the flexible electrical sensing probe to a contoured surface of the test body; and
   curing the encapsulation material to a state of reduced plasticity that produces the rigid electrical sensing probe permanently matched to the contoured surface of the test body;
   wherein the flexible sheet has a thickness of about 25 microns, the electrical coil is a copper coil with a thickness of about 17 microns, the ferrite powder comprises ferrite particles with a mean diameter of about 10 microns, and the encapsulation compound extends over a thickness of about 200-600 microns.

* * * * *